United States Patent [19]

Aranow et al.

[11] 4,147,160
[45] Apr. 3, 1979

[54] FOALING ALERT METHOD AND APPARATUS

[76] Inventors: Harold B. Aranow, 169 Windmill Rd., Willow Grove, Pa. 19090; Joseph P. Gyuraki, English Village Apts., Apt. C4, Bldg. 19, North Wales, Pa. 19454; Robert E. Warenius, 1160 Roberts Rd., Warminster, Pa. 18974

[21] Appl. No.: 815,993

[22] Filed: Jul. 15, 1977

[51] Int. Cl.² ............................................. A61B 5/10
[52] U.S. Cl. ................................. 128/2 S; 128/361; 340/573
[58] Field of Search .................. 128/2 R, 2 S, 2.1 A, 128/361; 340/573

[56] References Cited

U.S. PATENT DOCUMENTS

| 2,924,220 | 2/1960 | Von Micsky | 128/2 S |
| 3,520,294 | 7/1970 | Fuzzell et al. | 128/2 S |
| 3,768,459 | 10/1973 | Cannon et al. | 128/2 S |
| 3,782,368 | 1/1974 | Reibold | 128/2 S |
| 3,943,918 | 3/1976 | Lewis | 128/2.1 A |
| 4,055,839 | 10/1977 | Skeggs | 128/2 S |

*Primary Examiner*—William E. Kamm
*Attorney, Agent, or Firm*—Robert K. Youtie

[57] ABSTRACT

A foaling alert method and apparatus, specially developed and employed for use with mares wherein connector or coupling elements are forcibly separable and respectively attached to opposite exterior sides of the vulva or genital cavity, one of the coupling elements having an associated radio transmitter with a normally closed operating switch, the other coupling element engaging the operating switch in its coupled condition to open the switch, and the coupling elements being coupled before dilation of the cervix, such that upon dilation the coupling elements are separated to activate the transmitter which operates a remote alarm to signal an attendant.

8 Claims, 2 Drawing Figures

FOALING ALERT METHOD AND APPARATUS

BACKGROUND OF THE INVENTION

While there have, in the prior art, been provided a number of labor or contraction monitoring devices, such prior devices have been relatively complex in construction and operation, extremely expensive to manufacture and maintain, and not generally suitable for foaling by mares.

SUMMARY OF THE INVENTION

Accordingly, it is an important object of the present invention to provide a foaling alert or signalling device and method which is extremely simple in construction and practice, relatively inexpensive to manufacture so as to economically justify disposal after a single use, and which effectively provides a remote alerting signal which enables a veterinarian or other person in attendance to go about other work in another location without monitoring the mare until the onset of foaling when the attendant's presence is desired.

It is still another object of the present invention to provide a foaling alert method and apparatus having the advantageous characteristics mentioned in the preceding paragraph, which is extremely simple to practice and use, being substantially foolproof in operation, and entirely reliable even under abusive conditions of use.

Other objects of the present invention will become apparent upon reading the following specification and referring to the accompanying drawings, which form a material part of this disclosure.

The invention accordingly consists in the features of construction, combinations and arrangements of parts and method steps, which will be exemplified in the following description, and of which the scope will be indicated by the appended claims.

DESCRIPTION OF THE PREFERRED EMBODIMENT

Figure 1:
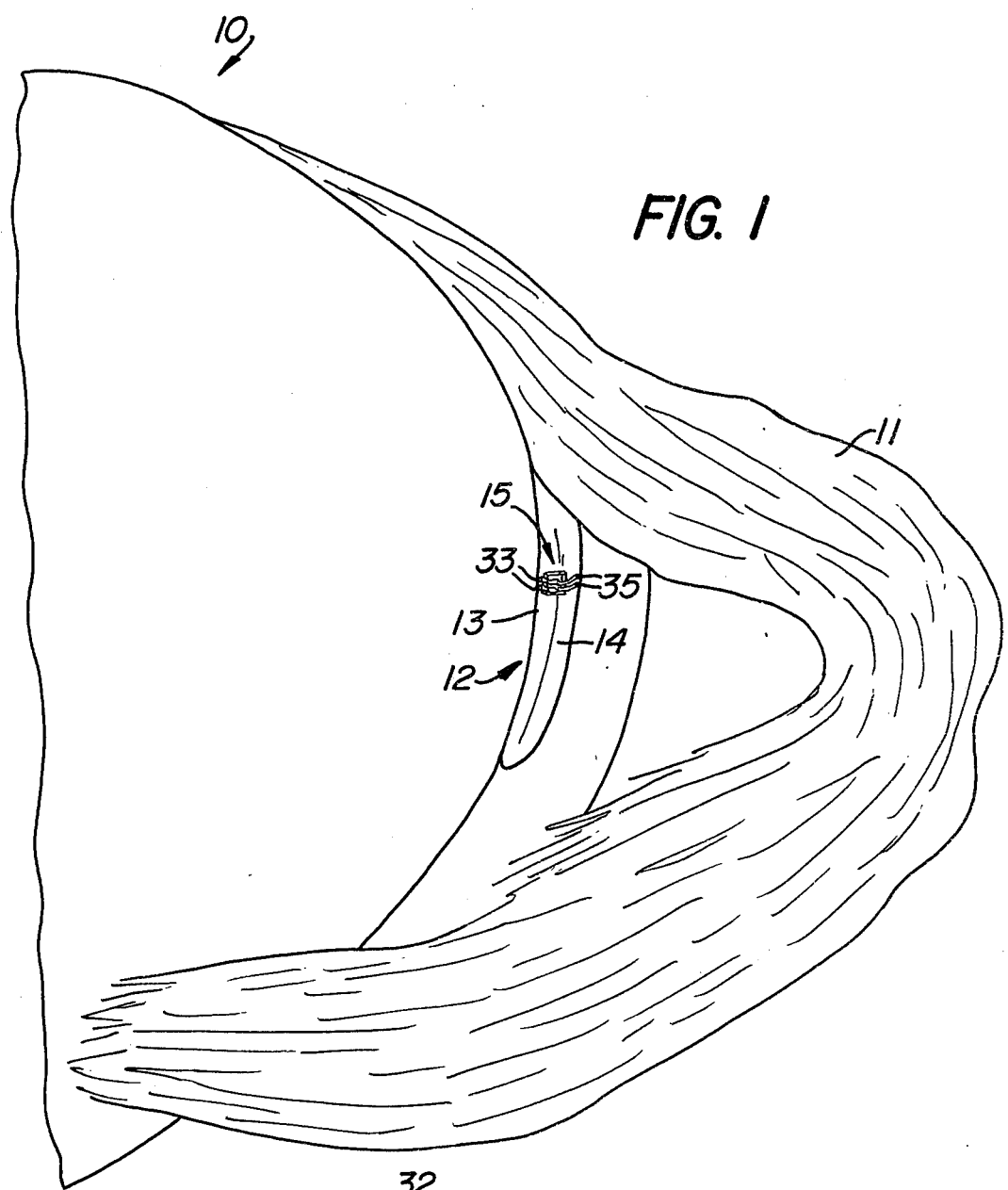
FIG. 1 is a partial rear perspective view showing a mare having a foaling alert device associated therewith in accordance with the teachings and practice of the instant invention.

Referring now more particularly to the drawings, and specifically to FIG. 1 thereof, there is shown a mare generally designated 10, in rear perspective view, the tail 11 being raised and exposing therebeneath the genital cavity or vulva 12.

Secured in position between opposite sides or external lips 13 and 14 of the vulva or genital cavity 12 is a signal or alert device 15 of the present invention.

Figure 2:
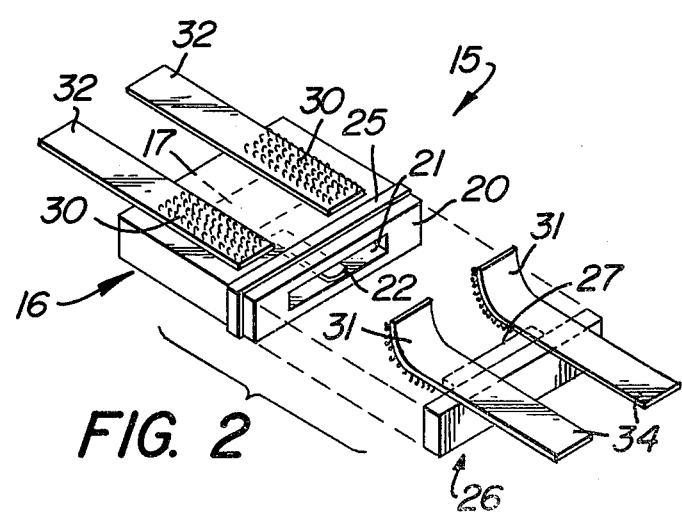
FIG. 2 is a perspective view showing the alert device, enlarged for clarity, apart from the mare and illustrating its separated or uncoupled alerting condition.

More specifically, the alert device or signal means 15 is shown in greater detail in FIG. 2, as including a housing 16, which may be provided internally thereof with a self-powered radio frequency transmitter 17. That is, by conventional techinques there is mounted in the housing 16 a miniature wireless transmitter 17, there being also contained in the housing 16 suitable power supply means, such as a miniature battery, or the like. The housing 16 may be a stainless steel case, or other suitably rugged sanitary construction. One end of the housing 16, as at 20, may be provided with a recess or opening 21, within which may be a switch actuating element or pin 22. That is, the transmitter 17 is provided with an operating switch, which switch is of a normally closed type, and includes suitable actuating means such as pin 22 which may be operated, as by depression into recess 21 to open the normally closed transmitter on-off switch. Suitable antenna means, such as external band 25 about housing 16 may serve to radiate a radio signal.

Complementary to the transmitter housing 16 and its recess 21, in facing spaced relation with respect to the housing face or end 20, there may be provided a switch operator, generally designated 26, movable into and out of facing engagement with housing end 20. Further, the switch operator 26 may include a protrusion or boss 27 facing toward the transmitter housing end 20 and configured for conforming insertion into housing recess 21 to engage and depress switch actuator pin 22 to open the transmitter operating switch. Thus, the switch operator 26 is movable into facing engagement with housing end 20, the lug 27 entering into recess 21 and depressing pin 22 to maintain the transmitter in an off or deactivated condition. This is the condition shown in FIG. 1.

Suitable means may be employed for retaining the switch operator 26 in its transmitter deactivating position toward the housing 16, which means may yield to a forcible separation of parts. One advantageous embodiment of such separable retaining means may be that of fastener fabric elements, such as is commonly sold under the trademark "Velcro", including a pile or loop fabric element and a hook fabric element for releasable holding interengagement of hooks and loops.

As best seen in FIG. 2, a pair of hook-type fastener fabrics 30 are secured in upwardly facing relation on the outer side or face of transmitter housing 16, as by adhesive or other suitable means. Secured to the switch operator 26 are a pair of complimentary pile-type fabric elements 31, extending beyond the switch operator for face-to-face complementary mating interengagement with respective hook fabric element 30 when the operator 26 is in position engaging the transmitter housing end 20 and entering recess 21. Thus, the complementary separable fastener fabric elements 30 and 31 serve to releasably retain the transmitter housing 16 and switch operator 26 in their fully engaged transmitter deactivated condition, while permitting of forcible separation to disengage switch operator 22 for activation of the transmitter.

Further, the fastener fabric elements 30 may be provided with attachment extensions or flexible sheet portions 32 extending away from the switch operator 26, which attachment extensions are adapted for attachment or securement to the mare on one side of the genital opening 12, say to one vulva lip 13, as by suturing 33 or other suitable securement means.

Similarly, the fabric fastener elements 31 are provided with flexible sheet extensions or attachment members 34 extending oppositely away from the housing 16 and adapted for suitable attachment to the other side of the genital cavity 12, say to vulva lip 14, as by sutures 35 or other suitable securement means.

Thus, by providing the hereinbefore described separable coupling elements 30 and 31, and associated transmitter and switch means 17, 22 and 27, secured to opposite sides of the female genital cavity in the coupled condition, all as illustrated in FIG. 1, the mare is prepared for foaling, whereupon a radio signal will be transmitted to a suitable remote receiver and alarm when it is essential for the attendant's presence.

From the foregoing it will now be understood that there is provided a method and apparatus for signalling the foaling of a mare, which is extremely simple in construction and operation, substantially foolproof in use, and does not in any way inhibit or disturb motion by the mare, and otherwise fully accomplishes its intended objects.

While the method and apparatus of the present invention have been primarily developed and employed for use with horses, and have been illustrated and described herein with particular reference thereto, it is appreciated that the instant invention is capable of use and advantageous results with many different animals, including cows, dogs and others, all of which uses are intended to be comprehended herein, the term "foaling" being considered to cover all such applications.

Although the present invention has been described in some detail by way of illustration and example for purposes of clarity of understanding, it is understood that certain changes and modifications may be made within the spirit of the invention.

What is claimed is:

1. A foaling alert device comprising a housing, a miniature wireless transmitter in said housing, normally closed switch means carried by said housing connected to said transmitter for activating and deactivating the latter, a switch operator movable toward said housing into switch opening engagement with said switch means and away from said housing out of engagement with said switch means to close the latter, attachment means connected to each of said housing and switch operator for attaching the same to respective sides of the female genital cavity, and separable retaining means secured to each of said housing and switch operator and releasably connected together to releasably retain said housing and switch operator toward each other in said switch opening engagement, for release of said retaining means and movement of said housing and switch operator away from each other to switch closing position upon opening of the genital cavity.

2. A foaling alert device according to claim 1, said housing having a recess removably receiving said switch operator, and said switch means being in said recess for switch opening engagement by said operator when the latter is in said recess.

3. A foaling alert device according to claim 1, said attachment means comprising flexible sheet members for securement to the external lips of the genital opening.

4. A foaling alert device according to claim 1, said separable retaining means comprising mating fastener fabrics extending from said housing and switch operator respectively for separable securement in overlying facing engagement when said housing and switch operator are toward each other.

5. A foaling alert device according to claim 4, said attachment means comprising flexible sheet extensions of said fastener fabric.

6. In the method of signalling the onset of foaling, the steps which comprise: providing a pair of forcibly separable coupling elements, securing respective coupling elements to opposite sides of a female genital cavity prior to dilation, associating with one coupling element a wireless transmitter having a normally closed on-off switch with the switch held open by the other coupling element when said coupling elements are coupled, and coupling said coupling elements, for separation of said coupling elements by dilation of the cervix to actuate said transmitter and effect a remote alarm.

7. The method according to claim 6, wherein said coupling elements are secured by suturing.

8. The method according to claim 6, wherein said coupling elements are coupled by placing fastener fabric parts in detachable facing engagement with each other.

* * * * *